United States Patent
George et al.

(10) Patent No.: US 11,166,998 B2
(45) Date of Patent: Nov. 9, 2021

(54) EURYCOMA LONGIFOLIA EXTRACT AND ITS USE IN ENHANCING AND/OR STIMULATING IMMUNE SYSTEM

(71) Applicant: Biotropics Malaysia Berhad, Shah Alam (MY)

(72) Inventors: Annie George, Puchong (MY); Yuuki Kawasaki, Yokyo (JP); Azreena Abas, Ampang (MY)

(73) Assignee: Biotropics Malaysia Berhad, Shah Alam Selangor (MY)

( * ) Notice: Subject to any disclaimer, the term of this patent is extended or adjusted under 35 U.S.C. 154(b) by 468 days.

(21) Appl. No.: 15/843,593

(22) Filed: Dec. 15, 2017

(65) Prior Publication Data
US 2018/0153950 A1  Jun. 7, 2018

Related U.S. Application Data

(62) Division of application No. 14/840,869, filed on Aug. 31, 2015, now abandoned.

(60) Provisional application No. 62/045,963, filed on Sep. 4, 2014.

(51) Int. Cl.
*A61K 36/185* (2006.01)
*A61P 37/00* (2006.01)

(52) U.S. Cl.
CPC ............ *A61K 36/185* (2013.01); *A61P 37/00* (2018.01)

(58) Field of Classification Search
CPC .................................................. A61K 36/185
See application file for complete search history.

(56) References Cited

U.S. PATENT DOCUMENTS 7,132,117 B2  11/2006  Sambandan et al.
2007/0009621 A1*  1/2007  Eng ....................... A61K 36/185
424/773

FOREIGN PATENT DOCUMENTS

CN  102911846 A  *  2/2013  .............. A61P 37/02

OTHER PUBLICATIONS

InformedHealth.org [Internet]. Cologne, Germany: Institute for Quality and Efficiency in Health Care (IQWiG); 2006. Using medication: Oral medications. Apr. 13, 2011 [Updated Aug. 10, 2017]. Available from: https://www.ncbi.nlm.nih.gov/books/NBK361020/ (Year: 2006).*

Ismail et al. "Randomized Clinical Trial on the Use of PHYSTA Freeze-Dried Water Extract *Eurycoma longifolia* for the Improvement of Quality of Life and Sexual Well Being in Men" Evidence-Based Complementary and Alternative Medicine vol. 2012, pp. 1-10, 2012.

Tambi "Standardized Water Soluble Extract of *Eurycoma longifolia* (LJ100) on Men's Health" International Journal of Andrology vol. 28, pp. 25-44, 2005.

Tongkat Ali_Physta_Performance Ingredients [online], [retrieved from the Internet on Mar. 2, 2017 5:34:37 PM]. URL:http://www.biotropicsingredients.com/physta.

* cited by examiner

*Primary Examiner* — Amy L Clark
(74) *Attorney, Agent, or Firm* — Cesari & McKenna, LLP

(57) ABSTRACT

A method for stimulating or enhancing the immune system with a composition that includes a *Eurycoma longifolia* aqueous extract. Also provided is a method for reducing the risk of infectious disease by administering the composition. Further disclosed is a method for treating an individual with a *Eurycoma longifolia* aqueous extract to increase the number of T-cells, improve Scoring of Immunological Vigor, lower immunological age, reduce fatigue, or alleviate or reduce stress.

9 Claims, 2 Drawing Sheets

EURYCOMA LONGIFOLIA EXTRACT AND ITS USE IN ENHANCING AND/OR STIMULATING IMMUNE SYSTEM

CROSS REFERENCE TO RELATED APPLICATIONS

This application is a divisional of U.S. patent application Ser. No. 14/840,869, filed on Aug. 31, 2015, which claims priority to U.S. Provisional Application No. 62/045,963, filed on Sep. 4, 2014. The content of these prior applications is hereby incorporated by reference herein in its entirety.

FIELD OF THE INVENTION

The present invention relates generally to the field of bioactive natural products. More particularly, the present invention relates to a composition derived from an extract of *Eurycoma longifolia* and its use in enhancing and/or stimulating the immune system.

BACKGROUND OF THE INVENTION

*Eurycoma longifolia* (commonly called tongkat ali or pasak bumi) is a herbal flowering plant in the family Simaroubaceae, native to the Southeast Asian region, including Malaysia, Indonesia, and, to a lesser extent, Thailand, Vietnam, and Laos. This plant is a shrub tree that grows up to 10 metres in height, with long leaves that are green in colour. The leaves are pinnate in shape (i.e., the leaflets are arranged in pairs). The flowers of this tree are dioecious, whereas its ovoid-shaped fruits will turn to dark brown colour when they are ripe.

*Eurycoma longifolia* is traditionally used for its aphrodisiac, anti-pyretic and anti-malarial effects. It is also consumed as a general tonic. The decoction of its long, woody root is taken orally to achieve these effects. It is also mixed with conventional food and beverage products as a nutritional additive. The benefits of the roots of Tongkat Ali include restoring energy and vitality, and enhancing blood flow and functioning after child birth. The leaves are used as a cure for malaria, ulcers, sexual transmitted diseases, gum diseases and insect bites.

*Eurycoma longifolia* is also well known among various ethnic groups for treating disease and enhancing health, particularly sexual health among men. Due to the high demand of *Eurycoma longifolia* for its tremendous health benefits, *Eurycoma longifolia* preparations are now widely available in the health-food market in the form of raw crude powder where the root is dried and grinded. *Eurycoma longifolia* is also available in the form of capsules which may either contain raw crude powder or standardised extract. *Eurycoma longifolia* extract is prepared by extracting the active ingredients, adjusting the preparation to a defined content of a constituent and followed by concentrating it to a standard level. Other than that, *Eurycoma longifolia* is available as an additive brewed with coffee and even canned processed drinks. It has been recommended that *Eurycoma longifolia* should be administered orally, as other means such as intraperitoneal could enhance its toxicity by approximately 100-fold.

A wide range of chemical compounds have been isolated, especially from the root of *Eurycoma longifolia*, which include eurycomanone, eurycomanol, eurycomalactone, canthine-6-one alkaloid, 9-hydroxycanthin-6-one, 14,15β-dihydroxyklaineanone, phenolic components, tannins, quanissoids, and triterpenes. Due to the presence of these chemical compounds, the root has been reported to have effective medicinal values in terms of sexual enhancement property for males, as well as antipyretic, antimalarial, antibacterial, and antitumor properties. *Eurycoma longifolia* has been well documented to exert antioxidative properties due to its high concentrations of superoxide dismutase (SOD). *Eurycoma longifolia* is famously known for its aphrodisiac effect, which is due to its ability to stimulate the production or action of androgen hormones, especially testosterone. Hence, it can be used as an alternative for testosterone replacement therapy in a variety of related conditions, for example, in the treatment of male osteoporosis due to androgen deficiency.

U.S. Pat. No. 7,132,117 broadly claims that an aqueous extract of *E. longifolia*, comprising a glycopeptide with a molecular weight of 4,300 daltons and having between 30 and 39 amino acids and sugar residues, has activity of increasing testosterone synthesis, increasing testosterone release from Leydig cells, increasing sperm count and increasing sperm motility. The composition of this extract is also claimed for the treatment of sexual dysfunction or male infertility.

To the best knowledge of the inventors, till date, there is no reliable disclosure on the effects of *Eurycoma longifolia* extracts on the immune system and its immuno-stimulatory effects. Hence, the present invention is focused on the effects of extracts of *Eurycoma longifolia* on the immune system and its immuno-stimulatory effects, which links to protecting humans and/or animals from infectious diseases, which may arise from bacterial or viral infections.

Extracts of *Eurycoma longifolia* as a result may potentially increase the immunity of individuals with decreased immunity as a result of a lifestyle of lack of sleep, stress and unbalanced meal and ageing. Immunomodulatory and enhancing effects would also be relevant in immune-compromised individuals such as those with cancer who run the risk of easier and rapid morbidity due to susceptibility to diseases as a result of reduced immunity arising from cancer treatment. This information will be useful and applicable for future researches on immune system and the development of a more comprehensive natural medicine approach to immune system-related diseases.

SUMMARY OF THE INVENTION

According to a first aspect of the present invention, there is provided the use of a composition comprising an effective amount of an extract of *Eurycoma longifolia* for the production of a preparation to stimulate and/or enhance the immune system/function.

In a preferred embodiment, the extract is an aqueous extract or a solvent extract.

In another preferred embodiment, the extract comprises the following active ingredients, in appropriate amounts:
  eurycomanone
  protein
  polysaccharide
  glycosaponin In also another preferred embodiment, the extract has an activity selected from the group consisting of:
  increasing the number of T-cells;
  improving Scoring of Immunological Vigor (SIV), a comprehensive index of overall immune function comprising of the optimal functioning of T-cells, CD4+/CD8+ ratio, Naive T-cell, Naive/Memory T-cell ratio, B cells, NK cells and T proliferative activity;

lowering the immunological age, which is a comprehensible form of immune function based on T-cell number and proliferative activity;
reducing fatigue; and
alleviating or reducing stress.

The above activities show that the *Eurycoma longifolia* extract enhances and/or stimulates the immune system/function and has an anti-aging effect, which leads to the protection of the body from infectious diseases, thus reducing morbidity arising from a compromised immune system, for example in a disease state such as with cancer and ageing.

According to a second aspect of the present invention, there is provided a composition comprising an effective amount of an extract of *Eurycoma longifolia* and a pharmaceutically or nutraceutically acceptable carrier to stimulate and/or enhance the immune system.

Preferably, the extract of *Eurycoma longifolia* is an aqueous extract or a solvent extract.

The extract comprises active ingredients, which include eurycomanone, protein, polysaccharide and glycosaponin in appropriate amounts.

The composition preferably having an activity selected from the group consisting of:
increasing the number of T-cells;
improving Scoring of Immunological Vigor (SIV), a comprehensive index of overall immune function;
lowering the immunological age, a comprehensible form of immune function based on T-cell number and proliferative activity;
reducing fatigue; and
alleviating or reducing stress.

According to a third aspect of the present invention, there is provided a method for treating an individual to achieve an outcome selected from the group consisting of increasing the number of T-cells, improving SIV (i.e. a comprehensive index of overall immune function), lowering the immunological age (i.e. a comprehensible form of immune function), reducing fatigue and alleviating or reducing stress, comprising administering to the individual an effective amount of an extract of *Eurycoma longifolia*.

The above-mentioned outcome enhances the immune function and has an anti-aging effect, which leads to protecting the body of the individual from infectious diseases.

The preparation of the present invention is provided in an acceptable carrier and can be administered by any method known to one of ordinary skill in the art such as powder, granule, tablet, capsule, aqueous medicine or injection.

The foregoing composition of an extract of *Eurycoma longifolia* can be formulated into various pharmaceutical or nutraceutical formulations for clinical use such as capsules including soft gel capsules, tablets, galenicals, powder, granules, aqueous medicine, injection and the like by standard methods, in which the active ingredients are present and administered as active component at an effective therapeutic amount based on its efficacy and toxicity, alone or in combination with other chemicals through various routes of administration such as oral, sublingual, intravenous, intramuscular and the like. The effective amount is sufficient to enhance and/or stimulate immunity, by way of increasing the number of T-cells.

The effective amount to enhance and/or stimulate immunity will depend on the severity of the condition being treated; individual patient parameters including age, physical condition, size and weight; concurrent treatment and drug interaction; frequency of treatment; and the mode of administration.

Preferably, the effective amount of the extract is 10 mg to 2,000 mg. More preferably, the effective amount is 200 mg to 400 mg.

DETAILED DESCRIPTION OF THE INVENTION

Figure 1:
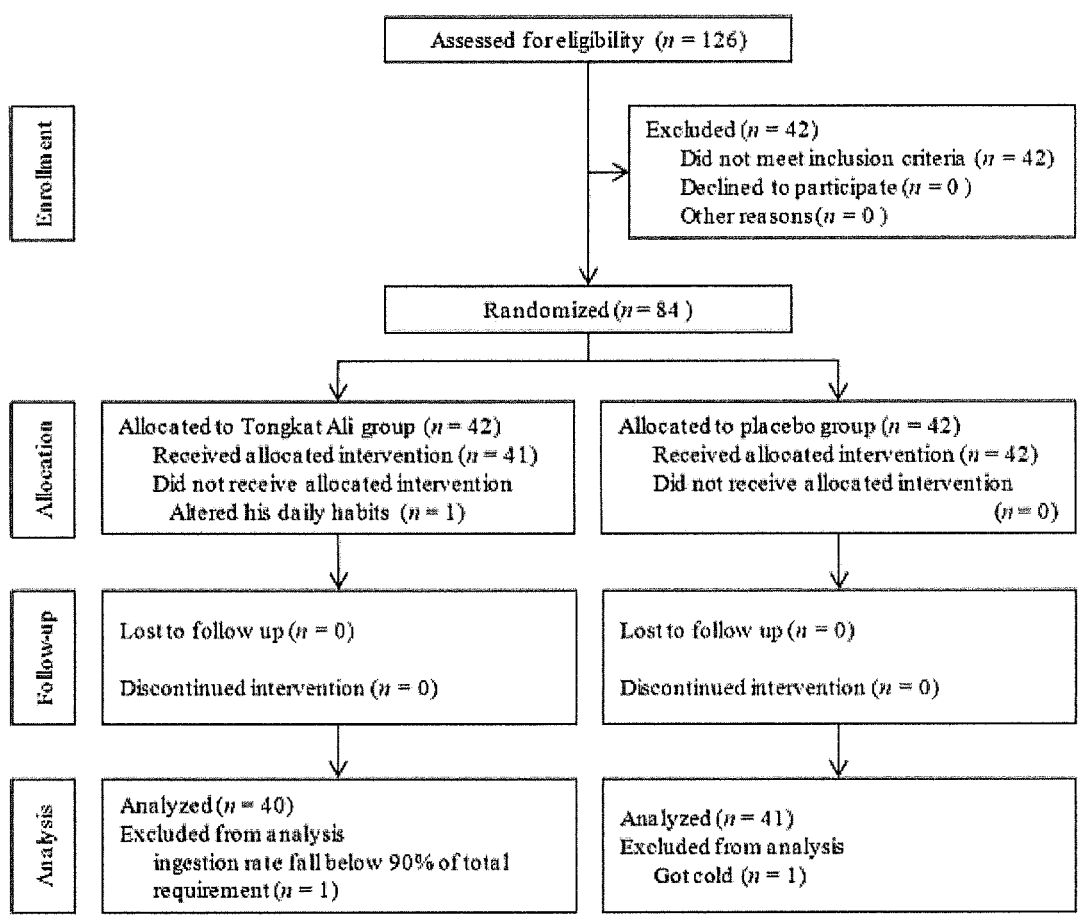
FIG. 1 is a flow chart of the study population, according to the present invention.

The present invention provides the use of a composition comprising an extract of *Eurycoma longifolia* in the enhancement and/or stimulation of the immune system/function.

The extract of *Eurycoma longifolia* as described herein contains the desired active ingredients from the *Eurycoma longifolia* plant preferably from the roots of *Eurycoma longifolia* plant, which may be further subjected to separation and characterization.

The extract is obtained by way of extraction procedures that are known in the art, which include the basic steps of pre-washing, drying or freeze-drying of the plant materials (e.g. root), grinding the plant materials to obtain a homogeneous sample and often improving the kinetics of analytic extraction and also increasing the contact of sample surface with a solvent system. Proper actions must be taken to assure that potential active ingredients/constituents are not lost, distorted or destroyed during the preparation of the extract from the *Eurycoma longifolia* plant sample.

The extract thus obtained may be ready for use as a medicinal agent in its original dry extract form, the form of tinctures and fluid extracts, it may be further processed to be incorporated in any dosage form such as tablets or capsules, or it may be fractionated to isolate individual chemical entities. Thus, standardization of extraction procedures contributes significantly to the final quality of the herbal drug.

In a preferred embodiment, the extract of *Eurycoma longifolia* is an aqueous extracts. The aqueous extract can be obtained by any known extraction method, for example boiling air-dried powdered plant part (e.g. roots) in water for approximately 10 minutes and then subjecting to cooling to room temperature. The aqueous extract is then filtered to remove particulate matter. The final volume of each filtrate can then be completed to 100 ml with distilled water with 0.2% Tween 80 to account for the evaporated water during boiling.

In another preferred embodiment, the extract of *Eurycoma longifolia* is a solvent extract. The solvent extract can be obtained from known extraction procedures using organic solvents. With the solvent extraction procedures, various plant substances, such as active ingredients, terpenoids and fatty acids, compounds can be separated depending on their solubility in different solvents. Examples of extraction solvents that can be utilized may be, for example butane, propane, ethanol, methanol, acetone, ethyl acetate, butyl acetate, carbon dioxide and nitrous oxide. Extraction with these organic solvents allows the whole plant extracts to be obtained or desired fractions of food and phyto-pharmaceutical quality without excessive production costs.

The extract of *Eurycoma longifolia* may also be prepared by other extraction methods that are known in the art, for example supercritical fluid extraction, cold press, and the like.

The extract of *Eurycoma longifolia* that is capable of enhancing and/or stimulating the immune system according to the present invention comprises the following active ingredients:

TABLE 1

| Ingredient | Amount (w/w) | Preferred amount (w/w) |
| --- | --- | --- |
| Eurycomanone | 0.3 to 3.5% | 0.8 to 2.5% |
| Total protein | more than 10% | more than 22% |
| Total polysaccharide | more than 20% | more than 30% |
| Glycosaponin | more than 30% | more than 40% |

In an embodiment, the *Eurycoma longifolia* extract is prepared by extracting the root of *Eurycoma longifolia* with water. The *Eurycoma longifolia* extract includes glycosaponins and eurypeptides. In some embodiments, the *Eurycoma longifolia* extract is prepared such that the extract comprises about 40% by weight glycosaponins and about 22% by weight eurypeptides. Eurypeptides are defined herein as peptides derived from *Eurycoma longifolia*. These peptides may be extracted, for example, by boiling pulverized *Eurycoma longifolia* root in water.

The composition of the present invention may be used to stimulate and/or enhance the immune system or function by increasing the number of T-cells, improving Scoring of Immunological Vigor, SIV (i.e. a comprehensive index of overall immune function) and lowering the immunological age, which is a comprehensible form of immune function based on T-cell number and proliferative activity, reducing fatigue and alleviating or reducing stress.

The immune system/function stimulation and/or enhancement effects of the *Eurycoma longifolia* extract of the present invention is evaluated using a method that is described in European patent publication number EP 2042867 A1 by Hirokawa. This evaluation method, which is defined herein as "Scoring of Immunological Vigor (SIV)", evaluates immunity by using immune cell markers for immune cells contained in sampled blood that comprises the step of determining an evaluation value for each of two or more selected kinds of immune cell markers based on the individual immune cell markers contained in the sampled blood, the step of adding the evaluation values so obtained for the at least two selected kinds of immune cell markers, and the step of evaluating the immunity from the results of the adding. Specifically, the method evaluates immunity by using a comprehensive index of overall immune function comprising of the optimal functioning of T-cells, CD4+/CD8+ ratio, Naive T-cell, Naive/Memory T-cell ratio, B cells, NK cells and T proliferative activity.

The present invention further provides a method for treating an individual to achieve an outcome selected from the group consisting of increasing the number of T-cells, improving SIV (i.e. a comprehensive index of overall immune function), lowering the immunological age (i.e. a comprehensible form of immune function), reducing fatigue and alleviating or reducing stress.

One embodiment of this method includes administering to the individual an effective amount of an extract of *Eurycoma longifolia*.

The extract of *Eurycoma longifolia* may be an aqueous extract or a solvent extract.

The effective amount to enhance and/or stimulate immunity will depend on the severity of the condition being treated; individual patient parameters including age, physical condition, size and weight; concurrent treatment and drug interaction; frequency of treatment; and the mode of administration.

Preferably, the effective amount of the extract is 10 mg to 2,000 mg. More preferably, the effective amount is 200 mg to 400 mg.

The above-mentioned outcome enhances the immune function and has an anti-aging effect, which leads to protecting the body of the individual from infectious diseases.

The term "infectious disease(s)" as described herein is defined as transmissible diseases or communicable diseases, comprise clinically evident illness (i.e., characteristic medical signs and/or symptoms of disease) resulting from the infection, presence and growth of pathogenic biological agents in an individual host organism.

The infections are normally caused by infectious agents such as viruses, viroids, and prions, microorganisms such as bacteria, nematodes such as roundworms and pinworms, arthropods such as ticks, mites, fleas, and lice, fungi such as ringworm, and other macroparasites such as tapeworms.

The infectious disease(s) mentioned herein can be organized into, but not limited to, the following six exposure categories and listed in typical descending order of risk. However, it must be noted that the sequence of exposure categories listed in individual country entries may vary according to local conditions.

i. food or waterborne diseases acquired through eating or drinking on the local economy, for example Hepatitis A, B, C and E, typhoid fever, etc.
ii. vector borne diseases acquired through the bite of an infected arthropod, for example Malaria, Dengue fever, Yellow fever, Japanese Encephalitis, African Trypanosomiasis, Cutaneous Leishmaniasis, Plague, Crimean-Congo hemorrhagic fever, rift Valley fever, Chikungunya, etc.
iii. water contact diseases acquired through swimming or wading in freshwater lakes, streams, and rivers, for example Leptospirosis, Schistosomiasis, etc.
iv. aerosolized dust or soil contact disease acquired through inhalation of aerosols contaminated with rodent urine, for example Lassa fever, etc.
v. respiratory disease acquired through close contact with an infectious person, for example Meningococcal meningitis, influenza, etc.
vi. respiratory-related diseases caused by infectious microorganisms, such as Nipah virus, Coronavirus, etc.
vi. animal contact disease acquired through direct contact with local animals, for example Rabies.

To assess the properties of the *Eurycoma longifolia* extract, a variety of experiments are performed using formulations of the extract. Details of the experiments are provided in the examples below.

In an embodiment, in addition to *Eurycoma longifolia* derived-compositions, e.g. extracts of *Eurycoma longifolia*, the preparation of the present invention includes a pharmaceutically or nutraceutically acceptable carrier for oral administration.

In order to facilitate oral administration, *Eurycoma longifolia* derived compositions may be mixed with any of a variety of pharmaceutically acceptable carriers for oral administration. By the term "pharmaceutically or nutraceutically acceptable carrier for oral administration" is meant a composition which is non-toxic, is not irritating to the human gastrointestinal system, and which can be mixed with *Eurycoma longifolia* derived compositions to form a solution, syrup, emulsion, gel, powdered mix or solid. Preparations for intravenous, intramuscular, subcutaneous or, in general, parenteral administration may also be produced by methods known in the art.

The pharmaceutically or nutraceutically acceptable carriers for oral administration may include, but not limited to sugars such as lactose, glucose and sucrose; starches such as corn starch and potato starch; cellulose and its derivatives, such as sodium carboxymethylcellulose, ethylcellulose, and cellulose acetate; powdered tragacanth; malt; gelatin; talc; stearic acid; magnesium stearate; calcium sulfate; vegetable oils such as corn oil, cotton seed oil, and olive oil; polyols such as propylene glycol, glycerine, sorbitol, mannitol, and polyethylene glycol; phosphate buffer solutions; cocoa butter; emulsifiers; as well as other non-toxic compatible substances used in pharmaceutical formulations. Wetting agents and lubricants such as magnesium stearate, as well as coloring agents, flavoring agents, excipients, tableting agents, stabilizers, antioxidants, and preservatives, can also be present. Other compatible pharmaceutical additives and actives may be included in the pharmaceutically acceptable carrier for use in the compositions of the present invention.

The preparations for oral administration may be in the form of tablets, caplets, soft and hard gelatine capsules, pills including delayed or slow or modified release formulations, dispersible powders or granules, lozenges, sachets, cachets, suspensions, emulsions, solutions, syrups, aerosols, and the like.

In other embodiments, in addition to *Eurycoma longifolia*-derived-compositions, e.g., extracts of *Eurycoma longifolia*, the preparations of the present invention include a pharmaceutically or nutraceutically acceptable carrier for topical application. Such pharmaceutically or nutraceutically acceptable carriers are well known in the art and, in essence, may include any currently used and commercially available dermatological or cosmetic preparation, or combinations thereof. Thus, one may simply modify an available dermatological or cosmetic preparation by adding a *Eurycoma longifolia*-derived composition and adjusting, as necessary, the ratios of its constituents to maintain a consistency suitable for a topical application.

As used herein, the term "pharmaceutically or nutraceutically acceptable carrier for topical application" means a composition suitable for topical application to human skin by spreading or rubbing, which does not cause irritation to human skin, and which can be mixed with *Eurycoma longifolia*-derived compositions to form a solution, emulsion, gel, lotion, ointment, balm, cream, or spreadable solid or paste. Such pharmaceutically acceptable carriers may include emollients, surfactants, humectants, lubricants, thickeners, waterproofing agents, bactericidal agents, percutaneous penetrating agents and preservatives. In addition, various cosmetic agents, such as fragrances and pigments may be included in a pharmaceutically acceptable carrier for topical application.

One embodiment where use of a composition for treating an individual to achieve an outcome selected from the group consisting of increasing the number of T-cells, improving Scoring of Immunological Vigor, SIV (i.e. a comprehensive index of overall immune function), lowering the immunological age (i.e. a comprehensible form of immune function), reducing fatigue and alleviating or reducing stress as described herein, is the administration to a subject an extract derived from *Eurycoma longifolia*.

The extract derived from *Eurycoma longifolia* may be an aqueous extract or a solvent extract.

The above-mentioned outcome enhances and/or stimulates the immune system/function and has an anti-aging effect, which leads to protecting the body of the individual from infectious diseases.

As used herein the subject is a human, non-human primate, cattle, horse, pig, sheep, goat, dog, cat, fish, prawn, chicken, rodent and many more. In all embodiments human subjects are preferred.

The term "infectious disease(s)" as described herein is defined as transmissible diseases or communicable diseases, comprise clinically evident illness (i.e., characteristic medical signs and/or symptoms of disease) resulting from the infection, presence and growth of pathogenic biological agents in an individual host organism.

The infections are normally caused by infectious agents such as viruses, viroids, and prions, microorganisms such as bacteria, nematodes such as roundworms and pinworms, arthropods such as ticks, mites, fleas, and lice, fungi such as ringworm, and other macroparasites such as tapeworms.

The infectious disease(s) mentioned herein can be organized into, but not limited to, the following six exposure categories and listed in typical descending order of risk. However, it must be noted that the sequence of exposure categories listed in individual country entries may vary according to local conditions.

i. food or waterborne diseases acquired through eating or drinking on the local economy, for example Hepatitis A, B, C and E, typhoid fever, etc.

ii. vectorborne diseases acquired through the bite of an infected arthropod, for example Malaria, Dengue fever, Yellow fever, Japanese Encephalitis, African Trypanosomiasis, Cutaneous Leishmaniasis, Plague, Crimean-Congo hemorrhagic fever, rift Valley fever, Chikungunya, etc.

iii. water contact diseases acquired through swimming or wading in freshwater lakes, streams, and rivers, for example Leptospirosis, Schistosomiasis, etc.

iv. aerosolized dust or soil contact disease acquired through inhalation of aerosols contaminated with rodent urine, for example Lassa fever, etc.

v. respiratory disease acquired through close contact with an infectious person, for example Meningococcal meningitis, influenza, etc.

vi. respiratory-related diseases caused by infectious microorganisms, such as Nipah virus, Coronavirus, etc.

vi. animal contact disease acquired through direct contact with local animals, for example Rabies.

In one embodiment of the present invention, a method for increasing the number of T-cells, improving Scoring of Immunological Vigor, SIV (i.e. a comprehensive index of overall immune function), lowering the immunological age (i.e. a comprehensible form of immune function), reducing fatigue and alleviating or reducing stress is disclosed which employs a preparation including a *Eurycoma longifolia*-derived composition that comprises the bioactive agent and is standardised to 0.3-3.5% eurycomanone, more than 10% total protein, more than 20% total polysaccharide and more than 30% glycosaponin. Preferably, the *Eurycoma longifolia*-derived composition comprising the bioactive agent is standardised to 0.8-2.5% eurycomanone, more than 22% total protein, more than 30% total polysaccharide and more than 40% glycosaponin.

In one embodiment, the preparation of *Eurycoma longifolia*-derived composition may be administered in conjunction with other medicaments known to those of skill in the art to increase the number of T-cells, improving SIV, lowering the immunological age, reducing fatigue and alleviating or reducing stress.

The *Eurycoma longifolia*-derived composition can be formulated and administered in effective amounts, alone or in a cocktail with other compounds. An effective amount is one sufficient to increase the number of T-cells, improving SIV, lower the immunological age, reduce fatigue and alleviate or reduce stress.

Effective amounts will depend, of course, on the severity of the condition being treated; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is the highest safe dose according to sound medical judgement.

Generally, daily doses of active compounds will be from about 10 milligrams per day to 2,000 milligrams per day. It is expected that oral doses in the range of 200 to 400 milligrams, in one or several administrations per day, will yield the desired results. In the event that the response in a subject is insufficient at such doses, even higher doses (or effective higher doses by a different, more localized delivery route) may be employed to the extent that patient tolerance permits. Dose ranges can be adjusted as necessary for the treatment of individual patients and according to the specific condition treated. Multiple doses per day are contemplated to achieve appropriate systemic levels of compounds.

The methods of the present invention may be practiced using any mode of administration that is medically acceptable, which produces effective levels of the active compounds without causing clinically unacceptable adverse effects. Such modes of administration include oral, rectal, topical, nasal, transdermal or parenteral routes. The term "parenteral" includes subcutaneous, intravenous, intramuscular, or infusion. Intravenous and intramuscular routes are not particularly suited for long term therapy and prophylaxis.

The compositions may conveniently be presented in unit dosage form and may be prepared by any of the methods well known in the art. In general, the compositions are prepared by uniformly and intimately bringing the active compounds into association with a liquid carrier, a finely divided solid carrier, or both, and then, if necessary, shaping the product.

Compositions suitable for oral administration may be presented as discrete units such as capsules, cachets, tablets, soft gels or lozenges, each containing a predetermined amount of the active compound. Other compositions include suspensions in aqueous liquors or non-aqueous liquids such as syrup or an emulsion.

The present invention will now be described in further detail by way of non-limiting examples.

Example 1

Preparation of *Eurycoma longifolia* Aqueous Extract

Aqueous extract of *Eurycoma longifolia* was prepared, characterised by comprising 0.8-2.5% eurycomanone, >22% total protein, >30% total polysaccharide and >40% glycosaponin, which was used to assess the immune-stimulatory and/or immune system enhancement activity of *Eurycoma longifolia*.

Method 1,000 kg Tongkat Ali wood chips was dried and grinded before being placed in a percolation tank. 5,000 L of purified water was filled in the tank, which was then heated up to 105° C.±10° C. The heated water was allowed to circulate and percolated through the tank for approximately 6 hours. The tank was then left for a few hours in order to allow settling solid materials contained therein. All the miscera was discharged through filters into the buffer tank for concentration. The miscera was concentrated by thin layer, heat and vacuum. The concentration process was continued until a concentrate of solid content of 20-30% was obtained. Then concentrate was then passed through a sterilizer. After sterilization, the concentrate was dried in a freeze-dryer. The dried concentrate was then milled into fine powders and mixed in a blender accordingly for standardization purposes. The extract was then utilised in bioactivity experiments as described in the following example.

Example 2

Immuno-Stimulatory Effect of *Eurycoma longifolia* Aqueous Extract

The aqueous extract of the root of *Eurycoma longifolia* was investigated for the immune-stimulatory effect in humans. The participants are healthy volunteers who feel fatigued daily and are between 40 and 59 years old. The effect of 4 weeks oral administration of the extract on participants' immunity was investigated.

Specifically, the aim of the study was to investigate whether *Eurycoma longifolia* has the following effects:
increases the number of T-cells
improves the Scoring of Immunological Vigor (SIV), which has been proposed as an index for expression of comprehensive immunity.
decreases the immunological age
reduce fatigue
alleviates or reduces stress

TABLE 2

| Study Design | |
| --- | --- |
| Basic design group trial | Double-blinded, randomized, placebo-controlled, parallel-group trial |
| No. of groups | 2 [Eurycoma longifolia/Tongkat Ali (TA)/Placebo (P)] |
| Number of ambulatory investigations: | 2 |
| Before starting ingestion | double as the screening test, week-0 |
| 4 weeks after starting ingestion | week-4 |
| Number of Participants Screened | N = 126 |
| Enrolled and assigned | n = 84 (TA: n = 42/P: n = 42) |
| Allocation ratio | 1:1 |

Materials and Methods
1. Study Site
The study institution, Seishin-kai Medical Association Takara clinic, is a community clinic in Japan. Data were collected and analyzed by Orthomedico Inc., in Japan.
2. Participants
Criteria for Eligibility, Screening, and Allocation
  i. Inclusion criteria
    a. Healthy adults who replied "Yes" to the selective "Yes/No" question "Do you feel fatigued daily?" at recruiting.

b. Persons whose ages are between 40 and 59 years
c. Low immunity score (SIV less than 23) on week-0's test
ii. Exclusion criteria
a. Persons who have previous medical history of heart failure and cardiac infarction.
b. Persons being treated for one of the following diseases: arterial fibrillation, cardiac arrhythmia, hepatic disorder, renal disorder, cerebrovascular disorder, rheumatism, dyslipidemia, hypertension, and other chronic diseases.
c. Persons who have taken medicine, herbal medicine, or dietary supplements within the preceding 30 days
d. Persons who have allergy
e. Pregnant women, lactating women, or women who want to get pregnant during the trial period
f. Pollinosis participants
g. Smokers
h. Persons who have been enrolled in other clinical trials within the last 3 months before the agreement to participate in this trial
i. Persons who the investigators judge as unsuitable to participate in the trial
iii. Selection criteria (at the screening test)
a. Persons who had relatively lower than normal scoring of immunological vigor (SIV) were selected (see Table 3)
iv. Allocation criteria
a. The mean values and SDs of SIV at baseline are not significantly different between TA and P groups

TABLE 3

Clinical and ecological definitions of Immunological Grade and SIV

| SIV | Immunological Grade | Definitions |
| --- | --- | --- |
| 24 | V | extremely high, ideal zone |
| 21-23 | IV | sufficiently high, safe zone |
| 17-20 | III | insufficient, observation zone |
| 13-16 | II | relatively low, warning zone |
| 8-12 | I | very low, critical zone which needs medical treatment |

Randomization
i. Allocation Procedure
The stratified randomization sequences were created with computer-generated random numbers using "Statlight #11 (Excel add-on by Yukms, Co. Ltd.). The inventors set and crossed the following 2 stratifications; sex (male or female) and age demographics (40's or 50's). Therefore, the following 4 strata were created; male-40's, male-50's, female-40's, and female-50's. Randomized sequences were created for each stratum. Finally, the inventors united the results of 4 randomizations, and assigned this union as the final randomization sequence for this trial.
These enrolling and allocating procedures were conducted by the key controller.
ii. Allocation concealment
a. Participants were blinded as to which group they were allocated by identical appearances of the test materials and by keeping the allocation information secret.
b. Physicians and clinical staffs were blinded by keeping the allocation information secret. They did not need to know the allocation information in order to handle the ambulatory investigations.
c. Statistical analysts were blinded by keeping the allocation information secret until they had finished the primary analyses.
As mentioned above, allocation and assignment procedures were conducted by the key controller. Allocation information was not disclosed until the statistical analysts had finished the primary analyses.

Sample Size
i. Determination of the sample size
Prior to finalizing the protocol, the inventors conducted a power analysis to determine a sufficient sample size using our previous data using the EZR package ver. 1.11 on R 2.13.0 with the following settings: statistical power as 80%, significant levels as $p<0.05$, the mean differences in changes of SIV between the 2 groups was ⅔ of their standard deviation, allocation ratio as 1:1.
The power analysis calculated that 36 participants were needed for each group. Therefore, the inventors assigned 42 participants to each group, considering dropouts and post-hoc deviation from the study protocol.

Management of Participants
i. Diary
Participants had to keep diaries during the ingesting period by filling out paper forms. They sent their diaries to the contact person for the operating authority every week.
ii. Before blood drawing, a history was taken in order to understand participants' health condition.
iii. The following compliance rules were presented to participants prior to obtaining their informed consent.
a. Participants cannot take any food and drink other than water within 6 hours before the blood drawing.
b. Participants must take their test materials according to the protocol.
c. Participants should not eat or drink excessively and should avoid extreme sexual activity; they should continue their everyday life and daily habits.
d. Participants must avoid taking any health foods, functional foods and dietary supplements other than the test material during the study period.
e. Participants must disclose to the clinic staff/investigator if they are on any medication (concomitant medication)*
f. Participants must avoid all other factors that might influence the outcome of the study, such as alcohol drinking and excessive exercise on the day before the outpatient investigation.
g. Should participants experience any adverse effect, they have to report it to the operator of this trial.

Withdrawal from the Trial.
Participants could withdraw from the trial whenever they wanted. If participants were thought to be in poor health or have behavioral problems, the investigator of the trial could stop their participation.
i. dropout
a. Participant wants to discontinue participation in the trial.
b. Participant stops participating in the trial.
c. Investigator stops continued participation because of heavy adverse events
d. Participant does not comply with the instructions of investigator and operating authority.
e. Participant does not comply with the lifestyle guidance during the trial.
f. Investigator decides to treat the subject as a dropout.
ii. discontinuation a. Investigator decides to discontinue an individual's participation because of heavy adverse events.
b. Investigator decides to discontinue participation because of objective symptoms.
c. Investigator decides to discontinue participation for other reasons.

3. Intervention
   (1) Test materials (see Table 4)
       i. TA group: Standardised freeze-dried Tongkat Ali/*Eurycoma longifolia* aqueous extract
       ii. P group: Placebo
   (2) Duration: 4 weeks
   (3) Dosage and administration
       Participants in each group took 1 capsule of the test material per day.
   (4) Supplier and Manufacturer
   The standardized extract to be investigated was produced by Biotropics Malaysia Berhad and test materials manufactured at Watanabe Pharmaceutical Co. Ltd. The batch number of the test materials in Watanabe Pharmaceutical was TA/306/8. The clinical trial was managed by Orthomedico, Inc, the operative authority of this trial.

TABLE 4

Ingredients in test materials

|  | *Eurycoma longifolia*/Tongkat Ali (TA) | Placebo (P) |
|---|---|---|
| Form | Capsule | Capsule |
| Raw materials | Physta ®, *Eurycoma longifolia* standardized root water extract: 200 mg<br>Sucrose esters of fatty acids: 30 mg | Rice powder: 200 mg<br>Sucrose esters of fatty acids: 30 mg |
| Active Ingredients | Eurycomanone Content:. 1.21% w/w<br>Total Protein: 26.3%<br>Total Polysaccharide: 28.8%<br>Glycosaponin: 46.2% | Eurycomanone Content<br>Total Protein: n.d.<br>Total Polysaccharide: 5.0%<br>Glycosaponin: 10.5% |
| Nets per capsule | 230 mg | 230 mg |

** Both test materials were filled in identical capsules so that there were no differences in appearance, taste and smell between materials in each group.
** n.d = not detected 4. Outcomes
   (1) Primary Outcomes: Immunological Parameters
       i. Immunological Parameters
           a. Positive and negative rates of subpopulations of T-cells determined with flow cytometry
              $CD3^+$, $CD4^+$, $CD8^+$, $CD4^+CD45RA^+$, $CD4^+CD45RA^-$, $CD8^+CD28^+$, $CD16^+CD56^+$, $CD3^-CD20^+$
           b. Numbers of T-lymphocyte subsets (using a. and differential count of leukocytes)
              T-cell, $CD4^+$T-cell, $CD8^+$T-cell, $CD4^+$ Naïve T-cell, $CD4^+$ Memory T-cell, $CD8^+CD28^+$ T-cell, B-cell, NK-cell
           c. Cell culture
              T-cell proliferative activity
           d. Calculated from the above and following parameters
              CD4/CD8 ratio, Naïve/Memory ratio, T-cell proliferative index, Immunological Age*, T-lymphocyte age, SIV*, Immunological Grade
              *The inventors focused especially on these two indexes.
   (2) Secondary Outcomes: Questionnaires
       i. Subjective Symptoms
           a. Japanese version of Profiles of Mood States (POMS), short ver.[6]
           b. Likert scales, which were originally developed
              Items: "I feel physically fatigued.", "I harass myself about sleeplessness.", "I feel hardly refreshed even though I have enough rest and sleep.", "Recently, I feel less happy", "My throat easily gets swollen.", "I easily get spots on my face, and my skin has serious roughness.", "I am often in a rotten mood because of feeling constipated.", "I often have diarrhea.", "I am easily irritated.", "I often feel flushed.", "I have a low sex drive.", "I feel unmotivated."
           Answer: This item . . . 1: does not fit me, completely. 2: hardly fits me. 3: really does not fit me. 4: slightly fits me. 5: somewhat fits me. 6: almost completely fits me.
   (3) Safety Parameters
       i. Physical examinations
          Height*, Weight, Body Mass Index, Percent Body Fat, Systolic Blood Pressure, Diastolic Blood Pressure, Pulse rate
          *Height was measured only once after informed consent was given.
       ii. Urinalysis**
           **collection quantity: approximately 25 ml.
           urine protein, urine glucose, urobilinogen, bilirubin, ketone bodies, pH, occult blood
       iii. Blood tests
           a. Collection condition
              Participant had fasted at least 6 hours prior to blood drawing.
              Approximately 25 ml of blood were collected, including samples for immunological assays.
           b. Hematological examinations
              White blood cell count (WBC), red blood cell count (RBC), hemoglobin, hematocrit, blood platelet count, mean corpuscular volume (MCV), mean corpuscular hemoglobin (MCH), mean corpuscular hemoglobin concentration (MCHC), leukocyte picture
           c. Biomedical examinations
              Aspartate aminotransferase (AST), alanine aminotransferase (ALT), gamma-glutamyl transpeptidase (γ-GTP), alkaline phosphatase (ALP), lactate dehydrogenase (LDH), leucine aminopeptidase (LAP), total bilirubin, direct bilirubin, indirect bilirubin, cholinesterase, zinc sulphate turbidity test (ZTT), total protein, urea nitrogen, creatinine, uric acid, creatine kinase (CK), calcium (Ca), sodium (Na), potassium (K), chloride (CI), inorganic phosphorus (IP), serum iron (Fe), serum amylase, total-cholesterol (T-cho), high-density lipoprotein cholesterol (HDL-cho), low-density lipoprotein cholesterol (LDL-cho), triglyceride (TG), free fatty acid, blood glucose, hemoglobin A1c (HbA1c, NGSP), glycoalbumin.

5. Analysis (1) Principle of analyses

The inventors employed the per-protocol principle instead of the intention-to-treat principle, considering the deviations from the protocol that were revealed post hoc.

(2) Primary Analysis

Statistical analyses were carried out to evaluate the null hypotheses that "Tongkat Ali did not have any effect on any endpoints". A 2-way MANOVA to estimate the effects of the following 2 factors: Intervention (between, 2: Tongkat-Ali, placebo) and Test period (within, 2: week-0, week-4) was conducted.

(3) Additional analyses i. Between-group comparison for changes.

To clarify whether the changes from week-0 to week-4 were different between the *Eurycoma longifolia* extract (TA) and placebo (P) groups, the inventors compared the changes in each outcome parameter using independent t-tests. Changes were calculated by subtracting the baseline value of each outcomes from the corresponding week-4 value.

ii. ANCOVA

To control the effects of baseline values and other confounding factors on outcomes, the inventors additionally conducted 1-way ANCOVA for primary and secondary outcomes. Although ANCOVA was not defined by the study protocol before starting this trial, ANCOVA seemed statistically more adequate than MANOVA to take baseline variations into consideration.

In ANCOVA for the full analysis set, the inventors set Intervention as an independent variable, values at week-4 of each outcome as dependent variables, and sex, age, and baseline values of each outcome as covariates. In addition, in ANCOVA for SEX stratification, the inventors set age and baseline values of each outcome as covariates, and independent variable and dependent variables were the same as in the full analysis set.

(4) Settings and Software

IBM SPSS ver. 18.0 was used for the analysis. A p value less than 0.05 in two-sided test was considered statistically significant.

Results

1. Study Population

A total of 83 of 84 participants completed the trial. One participant dropped out from the trial before starting ingestion, because this participant started dieting after the screening test, and this conflicted with a compliance rule of this trial. Two participants were excluded from the statistical analyses. One participant had a cold just before the week-4, which seemed to affect the immunological status. The other participant did not ingest enough of the test material in accordance with the trial protocol, and her ingestion rate fell below 90% of the total required ingestion. The flow chart of the study population is shown in FIG. 1.

Therefore, 81 participants were statistically analyzed. Baseline data on demographics, weight, BMI, immunological age, and SIV are shown in Table 5.

TABLE 5

Demographics and especially important indexes among primary endpoints at baseline (week-0)

|  | Participated | Screened | Analyzed |
|---|---|---|---|
| Total number | 126 | 84 | 81 |
| males | 64 | 42 | 41 |
| females | 62 | 42 | 40 |
| Age | 48.3 ± 5.3 | 48.3 ± 5.3 | 48.4 ± 5.3 |
| Race |  |  |  |
| Mongoloid | 126 | 84 | 81 |
| Nationality |  |  |  |
| Japanese | 126 | 84 | 81 |
| Job |  |  |  |
| employee | 57 | 40 | 38 |
| self-owned | 18 | 10 | 9 |
| SAHM | 38 | 24 | 24 |
| other | 13 | 10 | 10 |
| Marital history |  |  |  |
| married | 98 | 61 | 58 |
| single | 28 | 23 | 23 |
| Weight (kg) | 62.1 ± 13.3 | 60.8 ± 12.4 | 60.9 ± 12.3 |
| BMI (kg/m$^2$) | 22.8 ± 4.1 | 22.3 ± 3.8 | 22.4 ± 3.8 |
| Immunological Age | 51.8 ± 8.2 | 54.2 ± 6.9 | 54.3 ± 7.0 |
| SIV | 18.8 ± 2.1 | 17.9 ± 1.8 | 18.0 ± 1.8 |

SAHM: stay-at-home mom,
SIV: scoring of immunological vigor

2. Primary Analysis

Immunological Parameters

The results of Immunological Parameters are shown in Table 6. Many significant between-group differences were observed. Especially, the increased amount of SIV and Immunological Grade in *Eurycoma longifolia*/Tongkat Ali extract (TA) were significantly larger than those in placebo (P).

Similarly, the decrease in Immunological Age in TA was significantly larger than that in P. These trends were in a preferable direction. Additionally, the changed values of several items in TA were significantly larger than those in P; T-cell number, Naïve T-cell number, N/M ratio, B-cell number, and T-cell proliferative activity. These items are some of the components that make up SIV.

TABLE 6

Mean changes of immunological parameters at week-4 (n = 81)

| Item | Unit | Favorable Direction† | Tongkat Ali (n = 40) | Placebo (n = 41) | p-value** (t-test) |
|---|---|---|---|---|---|
| CD3$^+$ | % | — | 3.5 ± 4.6 | 2.4 ± 4.2 | 0.000 |
| CD4$^+$ | % | — | 4.2 ± 5.0 | 2.4 ± 4.6 | 0.000 |
| CD8$^+$ | % | — | −1.8 ± 2.9 | −2.2 ± 3.4 | 0.000 |
| CD4$^+$CD45RA$^+$ | % | — | 4.3 ± 7.6 | 3.2 ± 7.1 | 0.001 |
| CD4$^+$CD45RA$^-$ | % | — | −4.3 ± 7.6 | −3.2 ± 7.1 | 0.001 |

TABLE 6-continued

Mean changes of immunological parameters at week-4 (n = 81)

| Item | Unit | Favorable Direction† | Tongkat Ali (n = 40) | Placebo (n = 41) | p-value** (t-test) |
|---|---|---|---|---|---|
| CD8+CD28+ | % | — | 3.1 ± 12.4 | 5.1 ± 7.9 | 0.125 |
| CD3+CD20+ | % | — | −3.4 ± 3.5 | −2.7 ± 30 | 0.000 |
| CD16+CD56+ | % | — | 0.2 ± 3.0 | 0.0 ± 2.6 | 0.645 |
| Neutrophile | μl | — | −33.5 ± 1073.3 | 170.0 ± 973.3 | 0.845 |
| Lymphocyte | μl | — | 14.6 ± 247.2 | −111.8 ± 307.6 | 0.711 |
| T-cell | μl | H | 6.96 ± 206.1 | −51.7 ± 239.8 | 0.039 |
| CD4+ T-cell | μl | — | 80.0 ± 159.1 | −17.3 ± 148.1 | 0.003 |
| CD8+ T-cell | μl | — | −27.2 ± 65.0 | −64.6 ± 115.9 | 0.012 |
| CD4 CD8 ratio | — | rU | 0.4 ± 0.4 | 0.3 ± 0.5 | 0.000 |
| Naive T-cell | μl | H | 64.7 ± 88.5 | 16.9 ± 67.9 | 0.000 |
| Memory T-cell | μl | — | 15.3 ± 111.7 | −34.2 ± 106.8 | 0.392 |
| Naive Memory ratio | — | H | 0.1 ± 0.2 | 0.1 ± 0.2 | 0.000 |
| CD8+CD28+ T-cell | μl | H | −7.2 ± 65.1 | −21.9 ± 60.5 | 0.492 |
| B-cell | μl | H | −49.2 ± 66.5 | −51.9 ± 62.8 | 0.000 |
| NK-cell | μl | H | 2.4 ± 50.1 | −9.9 ± 50.3 | 0.766 |
| T-cell proliferative activity | — | H | 0.2 ± 0.2 | 0.2 ± 0.3 | 0.000 |
| T-cell proliferative index | — | H | 0.3 ± 0.4 | 0.2 ± 0.5 | 0.000 |
| Immunological Age | y.o. | L | −3.7 ± 5.6 | −2.0 ± 6.2 | 0.000 |
| T-lymphocyte Age | y.o. | L | 0.6 ± 4.9 | 1.3 ± 3.6 | 0.443 |
| SIV | — | H | 0.9 ± 1.9 | 0.0 ± 1.9 | 0.006 |
| Immunological Grade | — | H | 0.4 ± 0.6 | 0.1 ± 0.5 | 0.001 |

**p-values were calculated by independent t-test.
†H: higher is better, L: lower is better, rU: moderate is better (depicts the reversed U-shaped curve)

3. Subjective Symptoms

The results of POMS are shown in Table 7, and the results of the Likert scale are shown in Table 8. As for POMS, the changed scores of "Tension-Anxiety" and "Fatigue" in *Eurycoma longifolia*/Tongkat Ali extract (TA) were larger than those in placebo (P) with marginal significance, although a significant between-group difference was not observed.

As for Likert scales, remarkable differences compared to primary analyses were found. Significant between-group differences were observed in the following 3 items: "I feel physically fatigued", "I harass myself about sleeplessness", and "Recently, I feel less happy". The changes in these items in *Eurycoma longifolia*/Tongkat Ali extract (TA) were larger than those in placebo (P). "I feel hardly refreshed even though I have enough rest and sleep" showed a similar trend to the three items mentioned above, although the difference remained marginally significant.

TABLE 7

Comparisons of changes in POMS scores
Mean changes of POMS from week-0 to week-4 (n = 81)

| Item | Unit | Favorable Direction† | Tongkat Ali (n = 40) | Placebo (n = 41) | p-value** (t-test) |
|---|---|---|---|---|---|
| Tension - Anxiety | — | L | −7.2 ± 6.2 | −4.0 ± 8.2 | 0.057 |
| Depression | — | L | −4.6 ± 5.8 | −5.2 ± 7.8 | 0.686 |
| Anger - Hostility | — | L | −4.9 ± 6.5 | −2.8 ± 8.0 | 0.199 |
| Vigor | — | H | 5.3 ± 9.0 | 4.0 ± 6.5 | 0.486 |
| Fatigue | — | L | −10.0 ± 6.9 | −6.6 ± 9.5 | 0.067 |
| Confusion | — | L | −5.4 ± 6.6 | −6.0 ± 9.1 | 0.714 |

**p-values were calculated by independent t-test.
†H: higher is better, L: lower is better

TABLE 8

Comparisons of changes in scores of Likert scales
Mean changes of Likert scales from week-0 to week-4

| Item | Unit | Tongkat Ali (n = 40) | Placebo (n = 41) | p-value** (t-test) |
|---|---|---|---|---|
| I feel physically fatigued. | — | −1.3 ± 1.2 | −0.6 = 1.3 | 0.020 |
| I harass myself about sleeplessness. | — | −1.1 ± 1.2 | −0.4 = 1.4 | 0.019 |
| I feel hardly refreshed even though I have enough rest and sleep. | — | −1.5 ± 1.4 | −0.9 ± 1.5 | 0.082 |
| Recently, I feel less happy. | — | −0.8 ± 0.9 | −0.3 ± 1.1 | 0.042 |
| My throat easily gets swollen. | — | −0.6 ± 1.4 | −0.1 ± 1.6 | 0.195 |
| I easily got my spot on my face, and my skin has serious roughness. | — | −0.3 ± 1.4 | −0.4 ± 1.5 | 0.667 |
| I am often in a rotten mood because of feeling of constipation. | — | −0.8 ± 1.1 | −0.4 ± 1.5 | 0.271 |
| I often have diarrhea. | — | −0.2 ± 1.5 | −0.6 ± 0.9 | 0.221 |
| I am easily irritated. | — | −0.9 ± 1.3 | −0.5 ± 1.1 | 0.129 |
| I often feel flushed, and I easily get sweaty. | — | −1.0 ± 1.4 | −1.4 ± 1.4 | 0.182 |

TABLE 8-continued

Comparisons of changes in scores of Likert scales
Mean changes of Likert scales from week-0 to week-4

| Item | Unit | Tongkat Ali (n = 40) | Placebo (n = 41) | p-value** (t-test) |
|---|---|---|---|---|
| I have a low sex drive. | — | −0.6 ± 1.4 | −0.4 ± 1.5 | 0.731 |
| I feel unmotivated. | — | −1.0 ± 1.1 | −0.8 ± 1.3 | 0.370 |

**p-values were calculated by independent t-test.
†Lower score denotes that participants are in more preferable status.

4. Results According to ANCOVA Analysis Using the Full Analysis Set

Although t-tests and ANCOVA were additional analyses, the applicant reports mainly on the results of ANCOVA for the between-group comparisons. The reason is that ANCOVA is regarded as statistically more adequate than the two-way MANOVA, because ANCOVA takes the baseline variations into considerations.

4-1. Immunological Parameters

Figure 2:
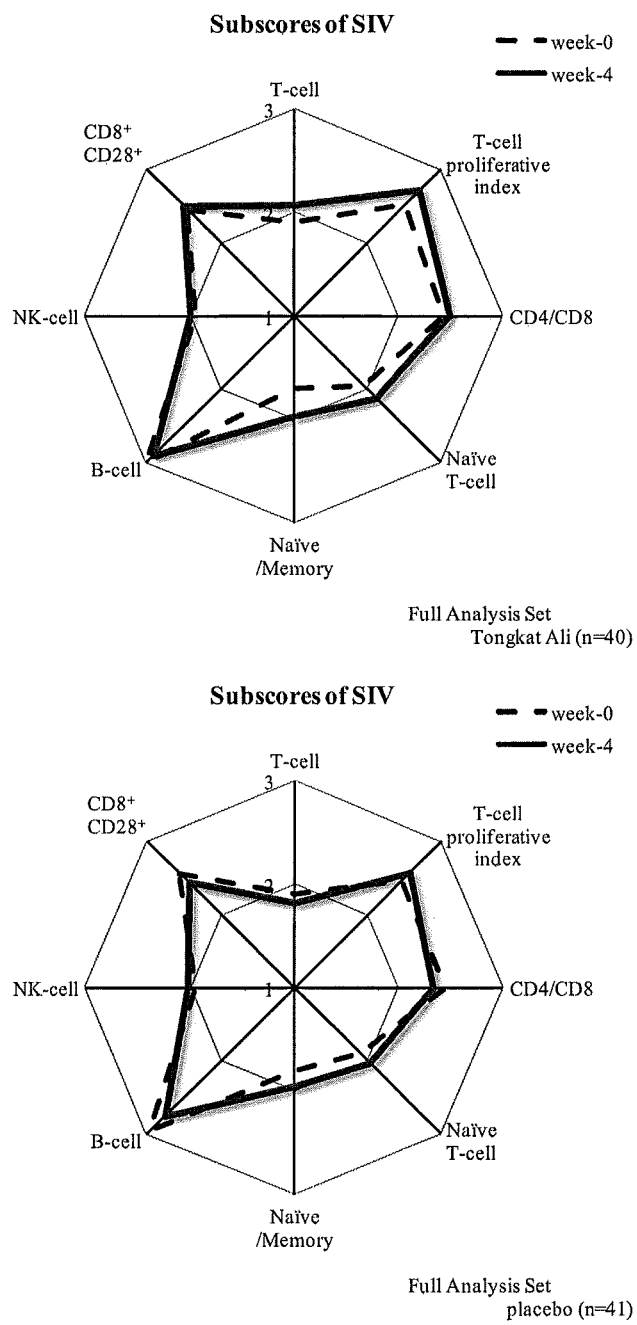
FIG. 2 illustrates sub-scores of SIV with ANCOVA analyses, according to the present invention.

The results of Immunological Parameters are shown in Table 9, and the sub-scores of SIV are shown in FIG. 2. Significant between-group differences were observed in SIV and Immunological Grade. These values in *Eurycoma longifolia*/Tongkat Ali extract (TA) were higher than those in placebo (P). In addition, participants in *Eurycoma longifolia*/Tongkat Ali extract (TA) showed relatively lower immunological age compared to participants in placebo (P), although the difference remained marginally significant. Among eight items, T-cell number and Naïve T-cell number were significantly larger in TA than in P.

TABLE 9

Between-group comparisons for immunological parameters in all participants using ANCOVA
Mean values of immunological parameters at week-4 within all participants (n = 81)

| Item | Unit | Favorable Direction† | Tongkat Ali (n = 40) | Placebo (n = 41) | p-value* (ANCOVA) |
|---|---|---|---|---|---|
| CD3⁺ | % | — | 75.6 ± 5.6 | 74.1 ± 7.4 | 0.231 |
| CD4⁺ | % | — | 48.7 ± 8.4 | 46.5 ± 8.1 | 0.177 |
| CD8⁺ | % | — | 24.6 ± 6.7 | 25.6 ± 7.6 | 0.638 |
| CD4⁺CD45RA⁺ | % | — | 39.3 ± 11.0 | 38.6 ± 12.2 | 0.498 |
| CD4⁺CD45RA⁻ | % | — | 60.7 ± 11.0 | 61.4 ± 12.2 | 0.498 |
| CD8⁺CD28⁺ | % | — | 66.1 ± 12.3 | 68.4 ± 13.8 | 0.285 |
| CD3⁺CD20⁺ | % | — | 9.7 ± 3.3 | 11.1 ± 5.0 | 0.107 |
| CD16⁺CD56⁺ | % | — | 10.5 ± 4.1 | 10.2 ± 4.7 | 0.636 |
| Neutrophile | μl | — | 3154.9 ± 1166.2 | 3317.3 ± 1152.8 | 0.415 |
| Lymphocyte | μl | — | 1512.0 ± 402.1 | 1403.1 ± 404.2 | 0.044 |
| T-cell | μl | H | 1144.6 ± 319.7 | 1031.2 ± 285.6 | 0.016 |
| CD4⁺ T-cell | μl | — | 741.7 ± 245.5 | 644.3 ± 187.9 | 0.009 |
| CD8⁺ T-cell | μl | — | 368.6 ± 132.0 | 362.6 ± 147.8 | 0.111 |
| CD4 CD8 ratio | — | rU | 2.2 ± 1.0 | 2.1 ± 1.0 | 0.996 |
| Naive T-cell | μl | H | 296.5 ± 142.1 | 244.3 ± 94.9 | 0.010 |
| Memory T-cell | μl | — | 445.2 ± 158.2 | 400.0 ± 153.0 | 0.058 |
| Naive Memory ratio | — | H | 0.7 ± 0.3 | 0.7 ± 0.4 | 0.732 |
| CD8⁺CD28⁺ T-cell | μl | H | 239.9 ± 87.2 | 240.6 ± 93.9 | 0.368 |
| B-cell | μl | H | 150.9 ± 75.3 | 161.5 ± 100.9 | 0.882 |
| NK-cell | μl | H | 155.5 ± 71.5 | 144.3 ± 78.2 | 0.189 |
| T-cell proliferative activity | — | H | 1.7 ± 0.2 | 1.7 ± 0.2 | 0.945 |
| T-cell proliferative index | — | H | 2.0 ± 0.6 | 1.7 ± 0.5 | 0.087 |
| Immunological Age | y.o. | L | 50.4 ± 8.5 | 52.5 ± 7.8 | 0.095 |
| T-lymphocyte Age | y.o. | L | 51.9 ± 7.5 | 51.3 ± 7.6 | 0.552 |
| SIV | — | H | 18.8 ± 2.4 | 18.0 ± 2.4 | 0.029 |
| Immunological Grade | — | H | 3.1 ± 0.8 | 2.8 ± 0.5 | 0.024 |

**p-values were calculated by ANCOVA.
†H: higher is better, L: lower is better, rU: moderate is better (depicts the reversed U-shaped curve)

4-2. Subjective Symptoms

The results of POMS are shown in Table 10, and the results of the Likert scale are shown in Table 11. As for POMS, no significant between-group difference was found. The mean value of Tension-Anxiety in *Eurycoma longifolia*/Tongkat Ali extract (TA) was lower than that in placebo (P), with marginal significance.

As for Likert scales, significant differences were shown in "I harass myself about sleeplessness" and "Recently, I feel less happy". Participants in TA showed relatively lower scores for these two items than did participants in P indicating better sleep and happier state on mind in the TA group.

TABLE 10

Between-group comparisons for scores of POMS in all participants using ANCOVA
POMS at week-4 within all participants (Normalized score, n = 81)

| Item | Unit | Favorable Direction† | Tongkat Ali (n = 40) | Placebo (n = 41) | p-value (ANCOVA) |
|---|---|---|---|---|---|
| Tension - Anxiety | — | L | 42.6 ± 7.9 | 44.5 ± 8.3 | 0.050 |
| Depression | — | L | 45.7 ± 7.3 | 44.7 ± 6.8 | 0.532 |
| Anger - Hostility | — | L | 45.4 ± 6.4 | 46.2 ± 7.4 | 0.207 |
| Vigor | — | H | 45.8 ± 8.6 | 46.2 ± 8.5 | 0.729 |
| Fatigue | — | L | 44.6 ± 8.2 | 45.2 ± 8.2 | 0.192 |
| Confusion | — | L | 46.7 ± 7.0 | 46.7 ± 6.6 | 0.865 |

**p-values were calculated by ANCOVA.
†H: higher is better, L: lower is better

TABLE 11

Between-group comparisons for scores of Likert scales in all participants using ANCOVA
Mean scores of Likert scales at week-4 within all participants (n = 81)

| Item | Unit | Tongkat Ali (n = 40) | Placebo (n = 41) | p-value* (ANCOVA) |
|---|---|---|---|---|
| I feel physically fatigued. | — | 3.1 ± 1.1 | 3.3 ± 1.0 | 0.117 |
| I harass myself about sleeplessness. | — | 1.9 ± 1.1 | 2.5 ± 1.3 | 0.007 |
| I feel hardly refreshed even though I have enough rest and sleep. | — | 3.0 ± 1.5 | 3.1 ± 1.1 | 0.363 |
| Recently, I feel less happy. | — | 2.2 ± 1.1 | 2.5 ± 1.1 | 0.034 |
| My throat easily gets swollen. | — | 2.4 ± 1.5 | 2.6 ± 1.2 | 0.306 |
| I easily got my spot on my face, and my skin has serious roughness. | — | 2.3 ± 1.3 | 2.4 ± 1.4 | 0.948 |
| I am often in a rotten mood because of feeling of constipation. | — | 2.5 ± 1.3 | 2.6 ± 1.2 | 0.347 |
| I often have diarrhea. | — | 2.4 ± 1.4 | 2.1 ± 1.1 | 0.217 |
| I am easily irritated. | — | 2.7 ± 1.3 | 2.8 ± 1.2 | 0.187 |
| I often feel flushed, and I easily get sweaty. | — | 2.2 ± 1.3 | 2.4 ± 1.4 | 0.868 |
| I have a low sex drive. | — | 3.2 ± 1.4 | 2.9 ± 1.2 | 0.519 |
| I feel unmotivated. | — | 2.6 ± 1.0 | 2.7 ± 1.1 | 0.455 |

*p-values were calculated by ANCOVA.
†Lower score denotes that participants is in more preferable status Discussion The primary aim of the present study is to assess the immune-stimulatory effects of *Eurycoma longifolia* extract/Tongkat Ali (TA) in humans. A total of 84 of 126 healthy volunteers passed the screening test, and 83 participants completed this trial.

The applicant conducted three kinds of statistical analyses to perform between-group comparisons. First, a two-way MANOVA was conducted, as a pre-selected statistical analysis outlined in the study protocol of this trial. Second, the changes from week-0 to week-4 between two groups using independent t-tests were recorded. Finally, the mean values at week-4 using one-way ANCOVA were compared, considering age, sex, and the baseline values of each index as covariates. Although t-tests and ANCOVA were additional analyses, the applicant reports mainly on the results of ANCOVA for the between-group comparisons. The reason is that ANCOVA is regarded as statistically more adequate than the two-way MANOVA, because ANCOVA takes the baseline variations into considerations.

Immunostimulatory Effects of *Eurycoma longifolia* Extract/Tongkat Ali (TA)

The results of the present trial indicate that the *Eurycoma longifolia* extract/Tongkat Ali extract has an immune-stimulatory effect in humans. SIV, a comprehensive index of overall immune function, improved significantly in participants on *Eurycoma longifolia* extract/Tongkat Ali (TA), and was significantly higher in TA than in placebo (P) at week-4, even if age, sex, and baseline value of SIV were considered. In addition, immunological age, which is an easily comprehensible form of immune function, was lower in TA than that in P. This shows that the immune function in TA was "younger" than that in placebo (P).

Hence, the *Eurycoma longifolia* extract/Tongkat Ali (TA) has possibly an anti-aging effect. These results suggest that the *Eurycoma longifolia* extract/Tongkat Ali enhances and/or stimulates the immune system/function in humans and, which might be linked to protecting the human body from the infectious diseases and infections in immune compromised individuals, such as those with cancer.

As for individual immunological components, the numbers of T-cells and naïve T-cells of participants in TA were significantly higher than those in P. The T-cell is one of the key components of adaptive and cell-mediated immunity, so, a higher T-cell number denotes a person's high immunological capacity, especially in adaptive, cell-mediated immunity. Adaptive immunity efficiently protects a human body from infectious pathogens antigens that have invaded it at least once in the past for acquisition of the immune memory before; Cell-mediated immunity protects humans from viruses and mutated cells. A naïve T-cell is an undifferentiated T-cell that has not been exposed to any antigens. That is, a naïve T-cell is related to the "acquisition" of the immune memory, and it plays an important role in adaptive immunity. Naïve T-cells protect human from "novel" antigens or pathogens, however, it deteriorates by aging or stress. Because these cells are well known to deteriorate with aging, Tongkat Ali (TA) would seem to have a preventive effect on aging of immunological function and stressed individuals.

Subjective Symptoms (POMS)

All items in POMS significantly changed between week-0 and week-4 in both groups. The scores of five negative items (Tension-Anxiety, Depression, Anger-Hostility, Fatigue, and Confusion) decreased at week-4 in both groups, and the one positive item, Vigor, increased. All these changes are preferable. Between-group comparisons using ANCOVA showed no differences in the full analysis set, however, Tension-Anxiety in the *Eurycoma longifolia* extract/Tongkat Ali (TA) was lower than in placebo (P), with marginal significance. These results suggest the possibility that ingestion of Tongkat-Ali improved the Tension-Anxiety more than did placebo, even if the age, sex and its baseline values were considered.

Subjective Symptoms (Likert Scale)

Many items were significantly improved within-groups, but these changes were observed more clearly in the *Eurycoma longifolia* extract/Tongkat Ali (TA). As for the between groups comparisons, items about sleeplessness and happy mood were more improved in TA compared to placebo (P), in the full analysis set. In summary, Tongkat Ali (TA) improved several subjective symptoms compared to placebo.

The results obtained herein indicate that the *Eurycoma longifolia* extract/Tongkat Ali (TA) has immune-stimulatory effects in humans, especially in adaptive, cell-mediated immunity assumed by the T-cell and its subsets. Although Tongkat Ali has been used traditionally as a revitalizer or antipyretic agent in Southeast Asia, its relationship with the immune function had not been investigated previously. Therefore, the results of this study are very important and meaningful because they have revealed for the first time the possible immune-stimulatory effects of Tongkat Ali in human, and might potentially allow inclusion of Tongkat Ali into the group of complementary medicines used for fatigue or infectious diseases. In addition, as it reduces immunological age, it may potentially also have anti-aging properties.

The invention claimed is:

1. A method of stimulating or enhancing the immune system, comprising administering to an individual in need thereof an effective amount of a composition that includes a *Eurycoma longifolia* aqueous extract.

2. The method of claim 1, wherein the extract contains, as active ingredients, eurycomanone, protein, polysaccharide, and glycosaponin.

3. The method of claim 2, wherein the extract contains, by weight, 0.3% to 3.5% eurycomanone, greater than 10% protein, greater than 20% polysaccharide, and greater than 30% glycosaponin.

4. The method of claim 3, wherein the extract contains, by weight, 0.8% to 2.5% eurycomanone, greater than 22% protein, greater than 30% polysaccharide, and greater than 40% glycosaponin.

5. The method of claim 1, wherein the effective amount is 10 mg to 2,000 mg.

6. The method of claim 5, wherein the effective amount is 200 mg to 400 mg.

7. The method of claim 1, wherein administering the extract improves Scoring of Immunological Vigor (SIV), lowers immunological age, reduces fatigue, or alleviates or reduces stress, and has an anti-aging effect.

8. The method of claim 7, wherein administering the extract improves SIV, the SIV being evaluated by measuring optimal functioning of T-cells, CD4+/CD8+ ratio, Naive T-cells, Naive/Memory T-cell ratio, B cells, NK cells, and T proliferative activity.

9. The method of claim 1, wherein the composition further includes a pharmaceutically or neutraceutically acceptable carrier.

* * * * *